United States Patent [19]

Mlot-Fijalkowski et al.

[11] 4,433,289
[45] Feb. 21, 1984

[54] METHOD FOR INSPECTING STEEL BILLETS WITH A DRY MIXTURE OF MAGNETIC PARTICLES AND A WATER SOLUBLE CARRIER SOLID

[75] Inventors: Adolf Mlot-Fijalkowski, Lincolnwood; Paul K. Borrows, Schaumburg, both of Ill.

[73] Assignee: Magnaflux Corporation, Chicago, Ill.

[21] Appl. No.: 225,312

[22] Filed: Jan. 15, 1981

[51] Int. Cl.$^3$ ............... G01N 27/84; G01R 33/12; H01F 1/28
[52] U.S. Cl. ............... 324/215; 252/62.52; 324/216
[58] Field of Search ............... 324/214–216; 252/62.52, 62.53

[56] References Cited

U.S. PATENT DOCUMENTS

| | | | |
|---|---|---|---|
| 2,267,999 | 12/1941 | Switzer | 175/183 |
| 2,936,287 | 5/1960 | Kazenas | 252/62.5 |
| 3,249,861 | 5/1966 | Pevar | 324/216 |
| 3,404,093 | 10/1968 | Borrows | 252/62.52 |
| 3,485,758 | 12/1969 | Borucki et al. | 252/62.52 |
| 3,609,532 | 9/1971 | Van Kirk | 324/215 |
| 3,897,990 | 8/1975 | Bjerke | 324/215 X |

FOREIGN PATENT DOCUMENTS

| | | | |
|---|---|---|---|
| 2244362 | 5/1974 | Fed. Rep. of Germany | 324/215 |

OTHER PUBLICATIONS

Mecana–Equipment for Detecting Cracks Facilitate the Targeted Elimination of Defects, Mecana SA, Machinery Works Brochure CH-8716 Schmerikon/Switz. pp. 1-8, Sep. 1976.
Pevar, Maxwell, "New Magnetic Test Includes Stainless Steels" Product Engineering Feb. 6, 1961, pp. 41–43.

Primary Examiner—Gerard R. Strecker
Attorney, Agent, or Firm—Hill, Van Santen, Steadman & Simpson

[57] ABSTRACT

A method and composition for non-destructive testing of magnetizable workpieces such as steel billets. A dry dispersion of ferromagnetic particles in combination with a fluorescent pigment and a water soluble carrier are deposited on the workpiece which is simultaneously or thereafter magnetized. The magnetizable particles are attracted to surface imperfections by the action of the magnetic field and become clustered therein to form indications. The indications are fixed more firmly to the piece by applying an aqueous spray, consisting either of a water mist or steam which activates the water soluble carrier so that upon drying, the indications remain firmly attached to the workpiece. Subsequent examination of the workpiece under ultraviolet irradiation enables the inspector to determine the extent and the location of the flaws.

5 Claims, 1 Drawing Figure

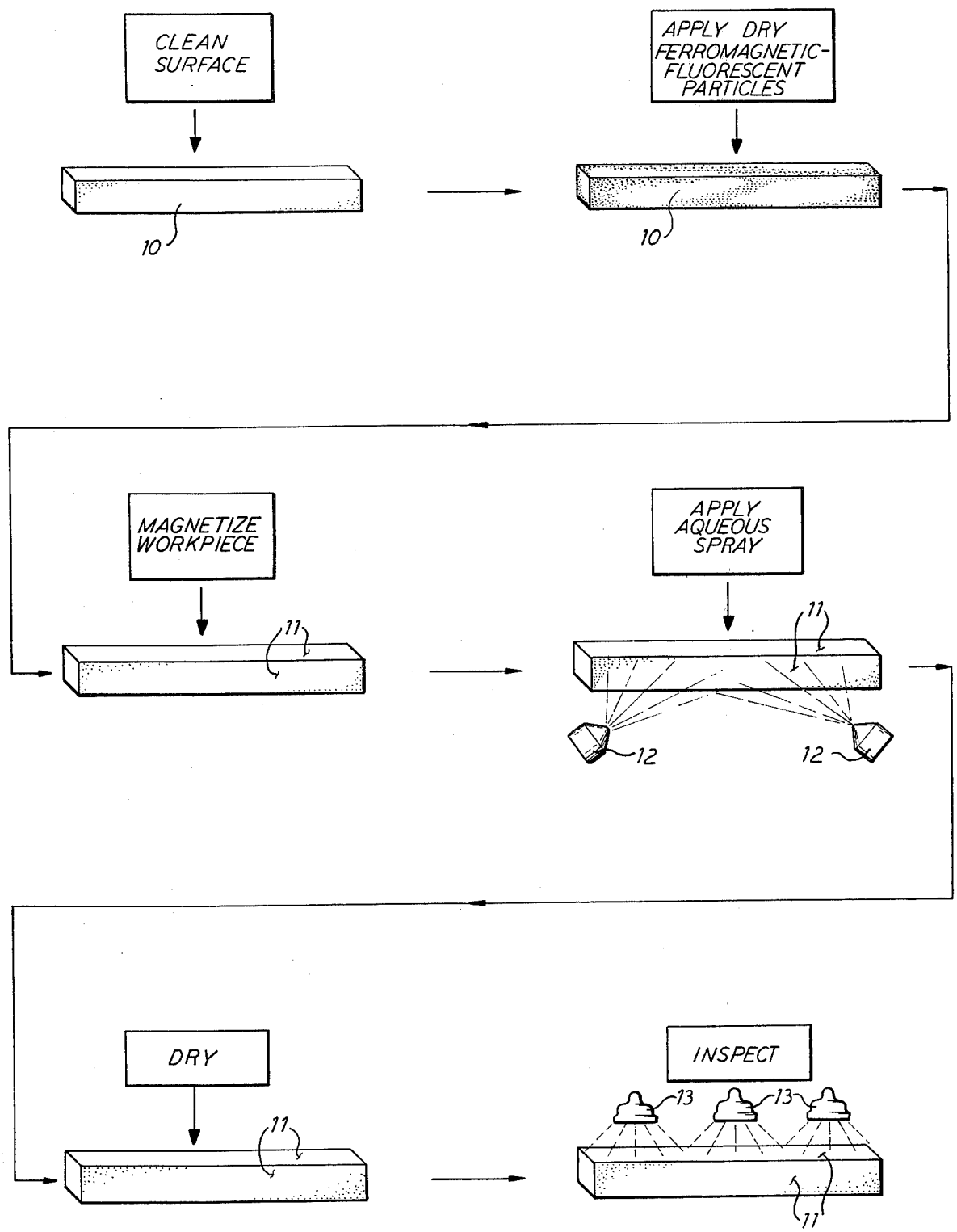

METHOD FOR INSPECTING STEEL BILLETS WITH A DRY MIXTURE OF MAGNETIC PARTICLES AND A WATER SOLUBLE CARRIER SOLID

BACKGROUND OF THE INVENTION

1. Field of the Invention

This invention is in the field of non-destructive testing by means of magnetic particle inspection. It seeks to provide a composition and a method which enable the indications to be held more firmly to the workpiece through the medium of including a water-sensitive binder material in the magnetic particle composition which is actuated by an aqueous spray to cause firm adherance of the indications to the workpiece.

2. Description of the Prior Art

Testing of magnetizable workpieces by means of magnetic particle inspection techniques is a highly developed art (see, for example, Metals Handbook, Eighth Edition, Volume 11, pages 44 to 74).

More recently, the magnetic particles have been combined with fluorescent particles either in the form of a water or oil suspension whereupon the workpiece was inspected under filtered ultraviolet or black light to observe any concentration pattern of fluorescent particles caused by a surface discontinuity. Prior art patents referring to this type of inspection technique include Switzer U.S. Pat. No. 2,267,999 and Kazenas U.S. Pat. No. 2,936,287. These patents relate, respectively, to lacquer bonded and resin bonded fluorescent magnetic particles for use in this type of inspection.

Methods of making fluorescent coated magnetic particles have also been described in U.S. Pat. Nos. 3,404,093 and 3,485,758, assigned to the assignee of the present application.

Fluorescent magnetic particle inspection is becoming increasingly important in the inspection of steel billets. Various defects can be detected in steel billets by using this inspection process. Discontinuities such as arrowhead cracks and longitudinal cracks are relatively easy to observe. Seams in the billet, however, pose a more serious problem. Seams are longitudinal discontinuities that appear as light lines in the surface of the steel. Normal seams are similar to longitudinal cracks, but produce lighter indications. Seams normally are closed tight enough that no actual opening can be visually detected without a magnetic particle inspection. Seams have a large number of possible origins, some mechanical and some metallurgical. Brush seams are clusters of short seams that give the appearance of having been painted or brushed onto the surface. Usually, these defects are the result of removal of metal from the steel surface by scarfing or scaling, exposing ingot blowholes and subsurface porosity. They may range in depth from about 0.005 to 0.300 inch and may occur either in zones or across the entire surface of the billet.

Laps are longitudinal discontinuities of varying severity that are caused by formation of ribs or extensions of metal during hot rolling and the subsequent folding over of these protrusions. Laps usually run at acute angles to the surface. Frequently, they occur at opposite sides of the billet, and very often run over the entire length of the billet.

Scabs appear as extraneous pieces of metal partially welded to the surface of a steel billet. The two major sources of scabs are splashing of metal against the mold wall during teeming, and adherence of scarfing wash or fins to blooms after conditioning.

One of the problems in conducting magnetic particle inspection of steel billets arises from the fact that the billets are subjected to relatively rough handling from the time the fluorescent magnetic particles are applied to the surface to the time they are inspected. Frequently, the handling is severe enough so that clusters of magnetic particles at a defect are broken loose from the surface of the workpiece and are not detected at the inspection station. Consequently, the inability of the indications to stay on the imperfection reduces the reliability of the test procedure.

SUMMARY OF THE INVENTION

The present invention provides a method and composition for inspecting a magnetizable workpiece wherein a dried composition containing magnetic particles, a fluorescent pigment, and a water-soluble carrier solid are applied to the surface of the piece and the workpiece is magnetized to cause the magnetic particles to adhere to surface imperfections thereby providing indications of the location of such imperfections. In order to fix the indications on the workpiece, an aqueous spray is applied to the indications, consisting of a spray of steam or a water mist. Upon drying of the workpiece, the carrier forms an adhesive bond between the fluorescent magnetic particles and the surface of the workpiece. The indications thus produced are much more resistant to handling than fluorescent magnetic particles currently being used.

BRIEF DESCRIPTION OF THE DRAWING

A method according to the present invention is illustrated schematically in the attached flowchart which illustrates a preferred embodiment.

DESCRIPTION OF THE PREFERRED EMBODIMENTS

In the attached drawings, a steel billet 10 is shown progressing through a series of operations which can be conveniently carried out at various work stations along a conveyor line. In the first station, the surface of the steel billet 10 is cleaned mechanically by abrading or the like to remove surface oxides and other foreign matter. At this stage, any moisture or oil which adheres to the billet 10 can be conveniently removed.

The next stage consists in applying a dry mixture of ferromagnetic and fluorescent particles to the steel billet 10. In making up the composition, magnetizable particles are combined with fluorescent pigment and a water-soluble carrier solid which has the property of being solubilized or activated by water so that upon drying, it has adhesive bonding properties. Natural gums such as gum acacia are particularly suitable for this purpose. The water-soluble carrier solid may also be an inorganic material such as sodium silicate or synthetic or natural water-soluble waxes, gums, or resins. While the proportions of the materials in the composition can vary widely, generally we prefer to use from 1 to 10% by weight of a water-soluble gum, 5 to 20% by weight of the fluorescent particles, and 50 to 90% by weight of ferromagnetic particles.

The ferromagnetic-fluorescent mixture in combination with the water-soluble binder may be applied by dusting or the like alone or in combination with a very lightweight dry diluent such as powdered silica or a silica aerogel.

The next step consists in magnetizing the workpiece by conventional means to form magnetic fields which attract the ferromagnetic particles and provide occulusions or indications such as diagramatically illustrated at reference numeral 11 representing a concentration of magnetic particles at a surface flaw. The size of the indications has been enlarged for purposes of clarity. Such occlusions provide indications of the existence of non-homogeneities and these indications must be preserved until such time as the piece can be inspected. In order to fix the indications on the workpiece, the next step consists in applying an aqueous spray through spray devices such as nozzles 12. The spray may consist of a mist of water or a spray of steam, since steam is readily available in steel making plants. The steam serves to activate or at least soften the water-soluble material contained in the dry particles so that upon a subsequent drying, as illustrated in the next step in the sequence, the indications 11 are held quite firmly against the surface of the piece. In this condition, they are no longer subject to easy removal by handling, and the billet can be stored in this condition pending later inspection. Such inspection is shown in the final step of the process wherein a bank of ultraviolet lights 12 is used to illuminate the surface of the billet rendering the indications 11 visible by the fluorescence of the fluorescent pigment attached to the ferromagnetic particles.

The following specific examples illustrate methods of making the improved indicating compositions of the present invention.

EXAMPLE I

Water-soluble gum acacia in an amount of 6 grams was dissolved in 100 ml of water. A fluorescent pigment was added in the amount of 11.5 gm. Then, 81.0 gm of pin grindings were added. Approximately 200 ml of isopropyl alcohol, containing 0.2 gm of "Uvitex OB" (a fluorescent whitener consisting of benzoxazole theophene) were added to precipitate the fluorescent magnetic particles from water. After drying and grinding, the dry powder was suspended in a silica aerogel and used in the magnetic particle inspection method mentioned above.

EXAMPLE II

Magnetic particles were added to a solution of water glass (sodium silicate, grade 0). To this mixture was added a water dispersion of a daylight fluorescent pigment. The mixture was blended thoroughly. A small quantity of isopropyl alcohol was added. The solids were then separated from the alcohol water solution and dried to provide an indicating composition which was rendered tacky by the application of a water mist.

The present invention provides an improved method for fixing fluorescent magnetic particles to the surface of a magnetizable workpiece. The fixation of the indications is obtained without the use of volatile solvents which require expensive recovery apparatus, and without the use of toxic materials. The application of the material is carried out in dry form so that it is completely applicable for use during winter months.

It should be evident that various modifications can be made to the described embodiments without departing from the scope of the present invention.

We claim as our invention:

1. A method for inspecting a magnetizable workpiece which comprises:
   applying to the surface of said workpiece a dry mixture of magnetic particles containing a fluorescent pigment adhered thereto and a water-soluble carrier solid capable of adhering to the surface upon activation by an aqueous medium,
   magnetizing said workpiece to cause the magnetic particles to adhere to surface imperfections while carrying the fluorescent pigment to such imperfections thereby providing indications of the location of such imperfections,
   applying an aqueous spray to said indications to activate said carrier solid into an adhesive bonding said particles to said imperfections, and
   drying the workpiece to cause setting of the activated adhesive and provide fluorescent pigment at such indications.

2. A method according to claim 1 in which said aqueous spray is a spray of steam.

3. A method according to claim 1 in which said aqueous spray is a water mist.

4. A method according to claim 1 in which said water-soluble carrier is a gum.

5. A method according to claim 1 in which said water-soluble carrier is sodium silicate.

* * * * *